United States Patent

Bernardi et al.

[11] 3,966,739
[45] June 29, 1976

[54] PYRROLE-CARBOXYLIC ACIDS LUMILYSERGOL ESTERS

[75] Inventors: Luigi Bernardi, Milan; Germano Bosisio, Palazzolo Milanese; Gian Carlo Fregnan, Milan, all of Italy

[73] Assignee: Societa Farmaceutici Italia S.p.A., Milan, Italy

[22] Filed: Mar. 7, 1972

[21] Appl. No.: 232,605

[30] Foreign Application Priority Data
Mar. 13, 1971 Italy.................................. 21713/71
Nov. 13, 1971 Italy.................................. 31059/71

[52] U.S. Cl............................. 260/285.5; 424/261
[51] Int. Cl.².................................... C07D 457/02
[58] Field of Search............ 260/285.5, 268 PE, 493

[56] References Cited
UNITED STATES PATENTS

| | | | |
|---|---|---|---|
| 3,155,667 | 11/1964 | Camerino et al. | 260/285.5 |
| 3,228,943 | 1/1966 | Bernardi et al. | 260/285.5 |
| 3,324,133 | 6/1967 | Arcamone et al. | 260/285.5 |
| 3,341,575 | 9/1967 | Fierce et al. | 260/493 |
| 3,418,360 | 12/1968 | Schulz et al. | 260/493 |
| 3,461,156 | 8/1969 | Fierce | 260/493 |
| 3,551,571 | 12/1970 | Pachter et al. | 260/309 |
| 3,704,233 | 11/1972 | Eich | 260/285.5 |

OTHER PUBLICATIONS

Temperilli et al., in Chem. Abstr., vol. 76, col. 14782n, (Jan. 1972), (abstracting Germany 2,112,273, 10/71).
Vitali et al., in Chem. Abstr., vol. 74, col. 110172t, (May 1971).
Tohroyama et al., Chem. Abstr., vol. 71, col. 50354e, 1969.

*Primary Examiner*—Alton D. Rollins
*Assistant Examiner*—Mary C. Vaughn
*Attorney, Agent, or Firm*—Hubbell, Cohen, Stiefel & Gross

[57] ABSTRACT

Esters of 1-methyl-lumilysergol-10-methylether having the formula:

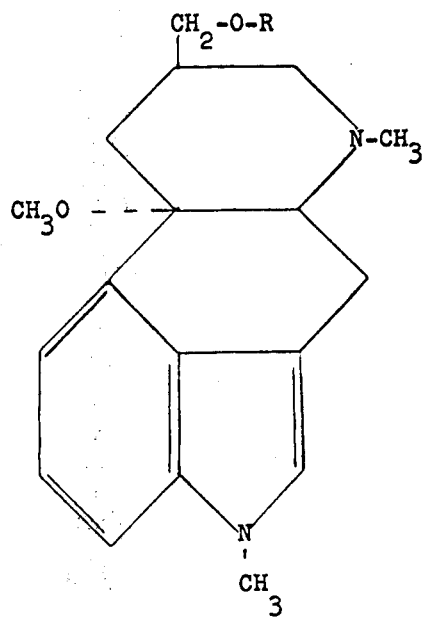

wherein R is selected from the group consisting of 2-furanoyl and the pyrrole group of the formula:

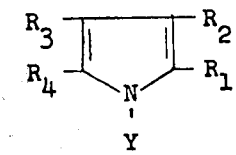

wherein Y is selected from the group consisting of hydrogen, lower alkyl having from 1 to 6 carbon atoms and phenyl; $R_1$ is selected from the group consisting of hydrogen, methyl and carbonyl; $R_2$ is selected from the group consisting of hydrogen, methyl, halogen and carbonyl, provided that only one of $R_1$ and $R_2$ can be carbonyl; $R_3$ and $R_4$ are selected from the group consisting of hydrogen, halogen, alkyl, alkoxy having from 1 to 6 carbon atoms and carboethoxy; the pharmaceutically acceptable addition salts thereof with an organic acid and a process for the preparation thereof. The compounds possess adrenolytic, hypotensive, sedative and antiserotoninic activities.

4 Claims, No Drawings

PYRROLE-CARBOXYLIC ACIDS LUMILYSERGOL ESTERS

The present invention relates to esters of 1-methyl-lumilysergol-10-methyl-ether having the formula:

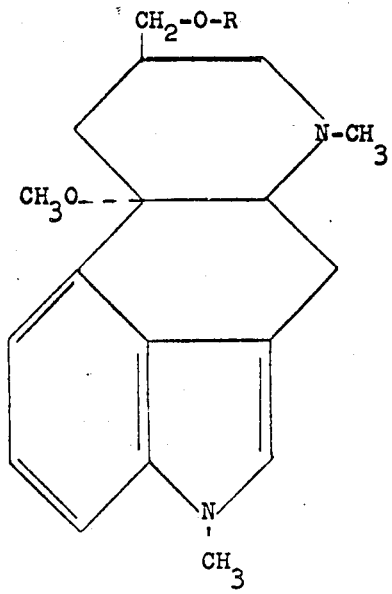

wherein R is selected from the group consisting of 2furanoyl and the pyrrole-group of the formula:

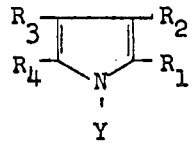

wherein Y is selected from the group consisting of hydrogen, lower alkyl having from 1 to 6 carbon atoms and phenyl; $R_1$ is selected from the group consisting of hydrogen, methyl and carbonyl; $R_2$ is selected from the group consisting of hydrogen, methyl, halogen and carbonyl, provided that only one of $R_1$ and $R_2$ can be carbonyl; $R_3$ and $R_4$ are selected from the group consisting of hydrogen, halogen, alkyl, alkoxy having from 1 to 6 carbon atoms and carboethoxy; the pharmaceutically acceptable addition salts thereof with an organic acid and a process for the preparation thereof.

The compounds of the invention have been proven to possess remarkable pharmacological activities as adrenolytic, hypotensive, sedative and antiserotoninic drugs. The process for preparing the compounds of the invention can be represented as follows:

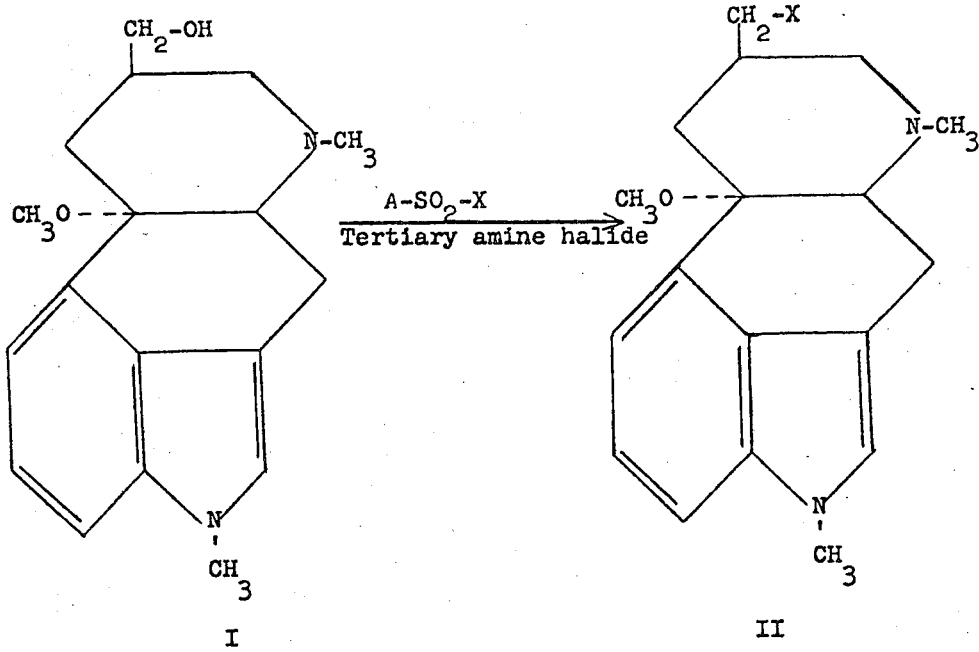

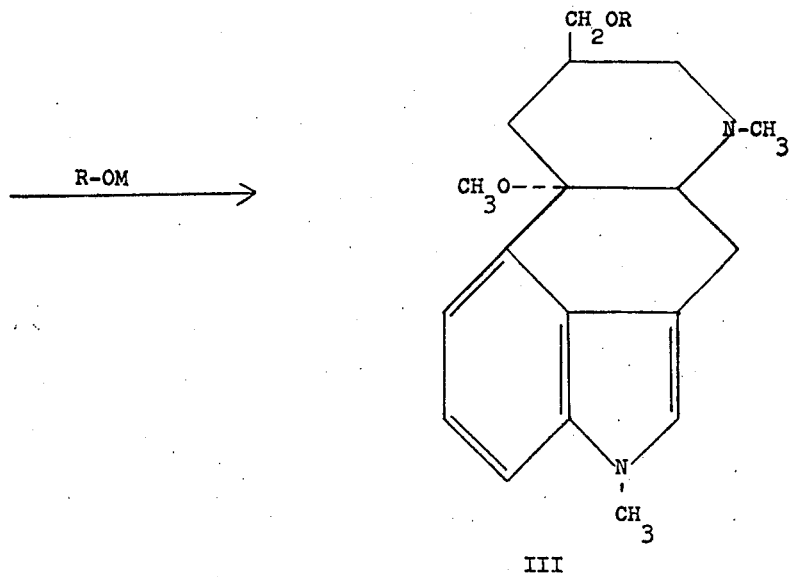
III
wherein A is lower alkyl or substituted or unsubstituted phenyl; X is chlorine or bromine; R is as described above and M is sodium or potassium.
U.S. Pat No. 3,228,943 of Bernardi et al describes and claims a process for the preparation of 1-methyl-lumilysergol-10-methyl-ether derivatives according to the scheme:
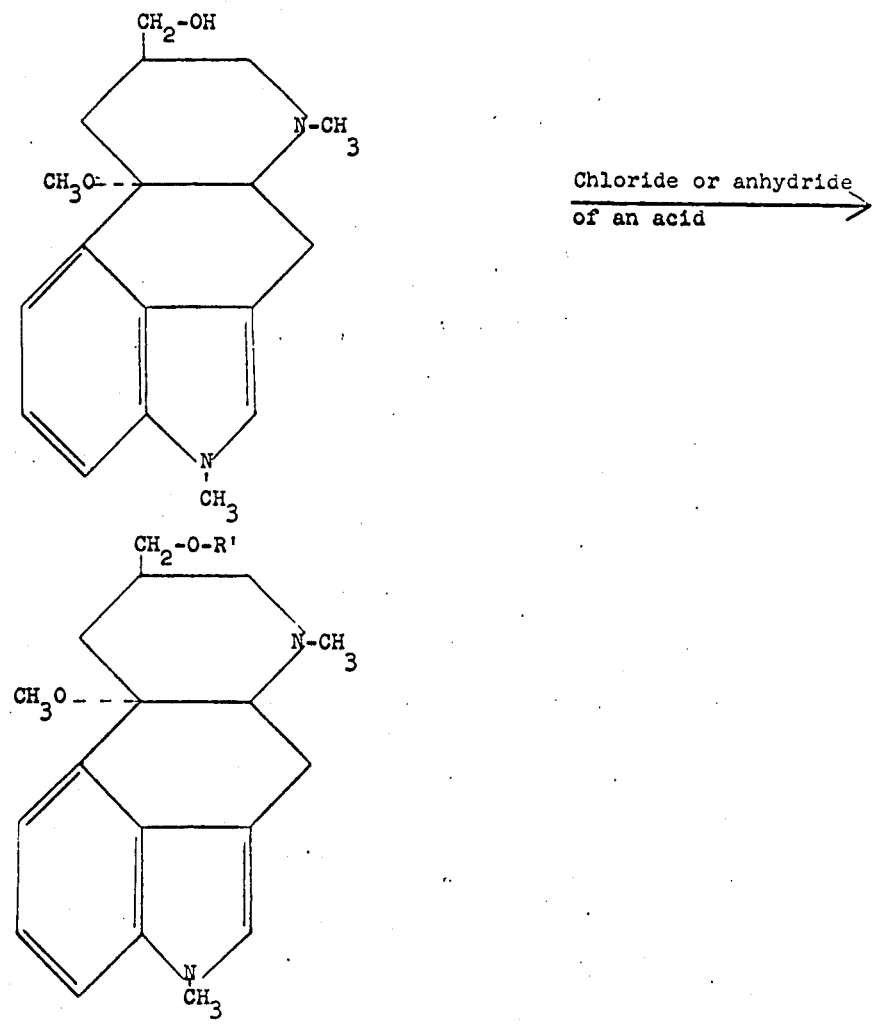

wherein R' is acyl. This process enables one to obtain a substantial number of esters employing different types of carboxylic acids.

A remarkable difficulty was noted, however, in transforming the acids containing the pyrrole- and furan-nucleus into the corresponding chlorides, since they are particularly unstable to the common chlorinating agents (phosphorus oxychloride and pentachloride, thionyl chloride).

It has now been found that the desired esters can be obtained by reacting a salt of the desired carboxylic acid with 1,6-dimethyl-10-methoxy-8-halomethylergoline. The 8-chloromethyl- or 8-bromomethyl-derivative is, preferably, employed.

The literature (Czech. Chem. Commun. 34, 2819-1969) describes a method for preparing 6-methyl-8-chloromethylergoline, but it has been proven that, under the conditions described, 1-methyl-8β-hydroxymethyl-10α-methoxy-ergoline does not give the corresponding chloro derivative, but on the contrary, tar-like products are obtained, the UV spectrum of which (λ max 352 nm) shows the absence of the chromophore group of ergoline and the possible presence of an ergolene resulting from the removal of the 10-methoxy group with the formation of an olefinic bond.

It has now been found that a hydroxyl group is easily replaced by a halogen atom and in high yields, by reacting 1,6-dimethyl-10-methoxy-8-hydroxy-methyl-ergoline with the chloride of an aryl- or alkyl-sulfonic acid, such as tosyl- or mesyl-chloride, in the presence of pyridine and of a certain quantity of a tertiary amine chloride, such as, for example, pyridinium chloride. The analogous bromo-derivative is obtained by employing the sulfonic acid bromide in the presence of pyridinium bromide. The thus obtained halogen derivative is dissolved in a polar aprotic solvent, such as for example, dimethylsulfoxide, and condensed with the salt of the desired acid and the reaction takes place over a period of from 3 to 10 hours and at a temperature between 40° and 150°C. The pharmaceutically acceptable addition salts of the compounds of the invention with an organic acid, such as maleic or tartaric acid, are obtained by reaction of the compound dissolved in an organic solvent with the desired acid in a known manner.

The adrenolytic activity of the compounds of the invention has been tested by employing dihydroergotamine as a comparison compound. Particularly, it has been determined on the isolated seminal small bladder of guinea-pig suspended in physiologic solution.

Table I reports the concentrations inhibiting 50% of the spasmogen action of adrenaline ($IC_{50}$).

TABLE I

| Compound | $IC_{50}$ (mcg/ml) |
|---|---|
| 1,6-Dimethyl-8β-(2'-pyrroyloxymethyl)-10α-methoxy-ergoline | 0.005 |
| 1,6-Dimethyl-8β/2'-(N.methyl)-pyrroyloxymethyl]-10α-methoxyergoline | 0.005 |
| 1,6-Dimethyl-8β-(3'-pyrroyloxymethyl)-10α-methoxy-ergoline | 0.005 |
| 1,6-Dimethyl-8β-(3',5'-dimethyl-2'-pyrroyloxymethyl)-10α-methoxyergoline | 0.05 |
| 1,6-Dimethyl-8β-(3',5'-dimethyl-4'-bromo-2'-pyrroyloxymethyl)-10α-methoxyergoline | 0.1 |
| 1,6-Dimethyl-8β-(3',5'-dimethyl-4'-carbethoxy-2'-pyrroyloxymethyl)-10α-methoxyergoline | 1.0 |
| 1,6-Dimethyl-8β-(1',3',5'-trimethyl-2'-pyrroyloxymethyl)-10α-methoxyergoline maleate | 0.01 |
| 1,6-Dimethyl-8β-(4'-methoxy-3'-pyrroyloxymethyl)-10α-methoxyergoline | 0.1 |
| 1,6-Dimethyl-8β-(2'-methyl-3'-pyrroyloxymethyl)-10α-methoxyergoline | 0.05 |
| 1,6-Dimethyl-8β-(2',4'-dimethyl-3'-pyrroyloxymethyl)-10α-methoxyergoline | 0.07 |
| Dihydroergotamine | 0.015 |

The same activity, in vivo, has been determined in the rat. Table II reports the doses $ID_{50}$ (in mg/kg) capable of reducing 50% of the lethal effects of adrenaline by intravenous administration (i.v.) and oral administration (os) of the compounds under examination.

TABLE II

| Compound | $ID_{50}$ (i.v.)(mg/kg) | (os)(mg/kg) |
|---|---|---|
| 1,6-Dimethyl-8β-(2'-pyrroyloxymethyl)-10α-methoxyergoline | 0.005 | 0.5 |
| 1,6-Dimethyl-8β-[2'-(N-methyl)-pyrroyloxymethyl]-10α-methoxyergoline | 0.025 | 1 |
| 1,6-Dimethyl-8β-(3'-pyrroyloxymethyl)-10α-methoxyergoline | 0.05 | 0.5 |
| 1,6-Dimethyl-8β-(3',5'-dimethyl-2'-pyrroyloxymethyl)-10α-methoxyergoline | 0.065 | 0.1 |
| 1,6-Dimethyl-8β-(3',5'-dimethyl-4'-bromo-2'-pyrroyloxymethyl)-10α-methoxyergoline | >1 | 0.5 |
| 1,6-Dimethyl-8β-(3',5'-dimethyl-4'-carbethoxy-2'-pyrroyloxymethyl)-10α-methoxyergoline | >0.1 | 2.5 |
| 1,6-Dimethyl-8β-(1',3',5'-trimethyl-2'-pyrroyloxymethyl)-10α-methoxyergoline maleate | 0.25 | 0.2 |
| 1,6-Dimethyl-8β-(4'-methoxy-3'-pyrroyloxymethyl)-10α-methoxyergoline | 0.075 | 0.3 |
| 1,6-Dimethyl-8β-(2'-methyl-3'-pyrroyloxymethyl)-10α-methoxyergoline | 0.05 | 0.25 |
| 1,6-Dimethyl-8β-(2',4'-dimethyl-3'-pyrroyloxymethyl)-10α-methoxyergoline | 0.1 | 0.7 |

TABLE II-continued

| Compound | ID$_{50}$ (i.v.)(mg/kg) | (os)(mg/kg) |
|---|---|---|
| Dihydroergotamine | 0.080 | 15 |

The following Examples are given to illustrate the preparation of the compounds of the invention without limiting it.

EXAMPLE 1

1,6-Dimethyl-8β-(2'-pyrroyloxymethyl)-10α-methoxyergoline 12.600 g of p-toluene-sulfochloride, dissolved over 50 cc of anhydrous pyridine were added, dropwise in 20 minutes, to a solution of 4.00 g of 1,6-dimethyl-8β-hydroxymethyl-10α-methoxyergoline and 6.00 g of pyridinium chloride in 50 cc of anhydrous pyridine heated to 45°C. Heating was continued at 45°–48°C for a further 4 hours and then the solvent was removed under vacuum. The residue, dissolved in 200 cc of chloroform, was washed with 10% sodium carbonate, and after drying, the solvent was eliminated by distillation under vacuum. The brownish foam was dissolved in chloroform, passed through a short chromatographic column containing 15 g of neutral aluminum oxide and then eluted with a small amount of chloroform.

Upon elimination of the solvent, a white foam was obtained, which by treatment with a little ether, was first dissolved and immediately after crystallizes. 3.630 g of white crystals of 1,6-dimethyl-8β-chloromethyl-10α-methoxyergoline were obtained melting at 140° – 142°C.

10.35 cc of sodium ethylate in ethanol (10 mg of sodium per cc) were added dropwise to a solution of 0.501 g of pyrrole-2-carboxylic acid in 30 cc of absolute ethanol. The solvent was removed immediately under vacuum. The sodium salt and 0.960 g of 1,6-dimethyl-8β-chloromethyl-10α-methoxyergoline dissolved in 45 cc of dimethylsulfoxide, were heated for 6 hours to 120°C. The reaction mixture was cooled and poured into 450 cc of water. The precipitate was washed with water and then dried. After decolorization in acetone and total removal of the solvent, the residue, taken up with ether, dissolved and immediately after crystallized. 860 mg of the product, melting at 225°–227°C, were obtained.

EXAMPLE 2

1,6-Dimethyl-8β-(3'-pyrroyloxymethyl)-10α-methoxyergoline

Operating as in Example 1, from 0.501 g of pyrrole-3-carboxylic acid and 0.960 g of 1,6-dimethyl-8β-chloromethyl-10α-methoxyergoline there was obtained 0.770 g of 1,6-dimethyl-8β-(3'-pyrroyloxymethyl)-10α-methoxyergoline melting at 222°–224°C.

EXAMPLE 3

1,6-Dimethyl-8β-(3',5'-dimethyl-2'-pyrroyloxymethyl)-10α-methoxyergoline

Operating as in Example 1, from 0.525 g of 3,5-dimethylpyrrole-2-carboxylic acid and 0.800 g of 1,6-dimethyl-8β-chloromethyl-10α-methoxyergoline, there was obtained 0.570 g of 1,6-dimethyl-8β-(3',5'-dimethyl-2'-pyrroyloxymethyl)-10α-methoxyergoline, melting at 176°–177°C.

EXAMPLE 4

1,6-Dimethyl-8β-[2'(N-methyl)-pyrroyloxymethyl]-10α-methoxyergoline

Operating as in Example 1, from 0.940 g of N-methylpyrrole-2-carboxylic acid and 1.600 g of 1,6-dimethyl-8β-chloromethyl-10α-methoxyergoline, there were obtained 1.170 g of 1,6-dimethyl-8β-[2'-(N-methyl)-pyrroyloxymethyl]-10α-methoxyergoline, melting at 80°–82°C.

EXAMPLE 5

1,6-Dimethyl-8β-(2'-furoyloxymethyl)-10α-methoxyergoline

Operating as in Example 1, from 0.615 g of 2-furoic acid and 0.670 g of 1,6-dimethyl-8β-chloromethyl-10α-methoxyergoline, there was obtained the above product melting at 141°–143°C.

Example 6

1,6-Dimethyl-8β-[2'-(N-ethyl)pyrroyloxymethyl]-10α-methoxyergoline 17.20 cc of sodium ethylate in ethanol (10 mg of sodium per cc) were dropped into a solution of 0.920 g of N-ethylpyrrole-2-carboxylic acid and 50 cc of absolute ethanol. Immediately thereafter the solvent was removed under vacuum, the sodium salt and 1.550 g of 1,6-dimethyl-8β-chloromethyl-10α-methoxyergoline dissolved in 85 cc of dimethylsulfoxide, were heated for 6 hours at 120°C. The reaction mixture was cooled and poured into 550 cc of water. The precipitate was washed with water and then dried. By decolorizing in acetone and removing all the solvent, the residue, taken up with ether, was dissolved and immediately thereafter crystallized. The product obtained melts at 70°–72°C, yield 86%.

EXAMPLE 7

1,6-Dimethyl-8β-[2'-(N-n.butyl)pyrroyloxymethyl]-10α-methoxyergoline maleate

Operating as in Example 6, but employing N-n.-butylpyrrole-2-carboxylic acid, there was obtained 1,6-dimethyl-8β-[2'-(N-n.butyl)pyrroyloxymethyl]-10α-methoxyergoline. The compound was then dissolved in acetone diluted with ether, and added with a maleic acid ethereal solution separately prepared (molar ratio 1:1). Under cooling, the salt precipitates in the crystalline form and melts at 86°–88°C. yield 68%.

EXAMPLE 8

1,6-Dimethyl-8β-[2'-(N-phenyl)pyrroyloxymethyl]-10α-methoxyergoline maleate

Operating as in Example 7, but employing N-phenylpyrrole-2-carboxylic acid, there was obtained 1,6-dimethyl-8β-[2'-(N-phenyl)pyrroyloxymethyl]-10α-methoxyergoline maleate, melting at 90°–92°C. Yield 73%.

EXAMPLE 9

1,6-Dimethyl-8β-[1'-methyl-3', 4', 5'-tribromo-2'-pyrroyloxymethyl]-10α-methoxyergoline maleate Operating as in Example 7, but employing 1-methyl-3,4,5-tribromopyrrole-2-carboxylic acid, there was obtained 1,6-dimethyl-8β-[1'-methyl-3',4',5'-tribromo-2'-pyrroyloxymethyl]-10α-methoxyergoline maleate, melting at 125°–130°C. Yield 75%.

EXAMPLE 10

1,6-Dimethyl-8β-[1'-methyl-3', 4'-dibromo-2'-pyrroyloxymethyl]-10α-methoxyergoline maleate Operating as in Example 7, but employing 1-methyl-3,4-dibromopyrrole-2-carboxylic acid, there was obtained 1,6-dimethyl-8β-[1'-methyl-3', 4'-dibromo-2'-pyrroyloxymethyl]-10α-methoxyergoline maleate, melting at 120°–122°C. Yield 68%.

EXAMPLE 11

1,6-Dimethyl-8β-[1'-methyl-5'-bromo-2'-pyrroyloxymethyl]-10α-methoxyergoline maleate Operating as in Example 7, but employing 1-methyl-5-bromopyrrole-2-carboxylic acid, there was obtained 1,6-dimethyl-8β-[1'-methyl-5'-bromo-2'-pyrroyloxymethyl]-10α-methoxyergoline maleate, melting at 115°–118°C. Yield 50%.

EXAMPLE 12

1,6-Dimethyl-8β-[3', 4', 5'-trichloro-2'-pyrroyloxymethyl]-10α-methoxyergoline

Operating as in Example 6, but employing 3,4,5-trichloropyrrole-2-carboxylic acid, there was obtained 1,6-dimethyl-8β-[3', 4', 5'-trichloro-2'-pyrroyloxymethyl]-10α-methoxyergoline, melting at 200°–202°C. Yield 47%.

EXAMPLE 13

1,6-Dimethyl-8β-[3',4'-dichloro-2'-pyrroyloxymethyl]-10α-methoxyergoline

Operating as in Example 6, but employing 3,4-dichloropyrrole-2-carboxylic acid, there was obtained 1,6-dimethyl-8β-[3', 4'-dichloro-2'-pyrroyloxymethyl]-10α-methoxyergoline, melting at 205° – 207°C. Yield 54%.

EXAMPLE 14

1,6-Dimethyl-8β-[5'-chloro-2'-pyrroyloxymethyl]-10α-methoxyergoline maleate

Operating as in Example 7, but employing 5-chloropyrrole-2-carboxylic acid, there was obtained 1,6-dimethyl-8β-[5'-chloro-2'-pyrroyloxymethyl]-10α-methoxyergoline maleate, melting at 123° – 125°C. Yield 60%.

EXAMPLE 15

1,6-Dimethyl-8β-[3', 5'-dimethyl-4'-bromo-2'-pyrroyloxymethyl]-10α-methoxyergoline Operating as in Example 6, but employing 3,5-dimethyl-4-bromopyrrole-2-carboxylic acid, there was obtained 1,6-dimethyl-8β-[3',5'-dimethyl-4'-bromo-2'-pyrroyloxymethyl]-10α-methoxyergoline, melting at 135° – 138°C. Yield 62%.

EXAMPLE 16

1,6-Dimethyl-8β-[2', 4'-dimethyl-5'-carbethoxy-3'-pyrroyloxymethyl]-10α-methoxyergoline Operating as in Example 6, but employing 2,4-dimethyl-5-carbethoxy-pyrrole-3-carboxylic acid, there was obtained 1,6-dimethyl-8β-[2', 4'-dimethyl-5'-carbethoxy-3'-pyrroyloxymethyl]-10α-methoxyergoline, melting at 116° – 118°C. Yield 46%.

EXAMPLE 17

1,6-Dimethyl-8β-[3', 5'-dimethyl-4'-carbethoxy-2'-pyrroyloxymethyl]-10α-methoxyergoline Operating as in Example 6, but employing 3,5-dimethyl-4-carbethoxy-pyrrole-2-carboxylic acid, there was obtained 1,6-dimethyl-8β-[3', 5'-dimethyl-4'-carbethoxy-2'-pyrroyloxymethyl]-10α-methoxyergoline, melting at 120°–122°C. Yield 54%.

EXAMPLE 18

1,6-Dimethyl-8β-[1', 3',5'-trimethyl-2'-pyrroyloxymethyl]-10α-methoxyergoline maleate Operating as in Example 7, but employing 1,3,5-trimethylpyrrole-2-carboxylic acid, there was obtained 1,6-dimethyl-8β-[1', 3', 5'-trimethyl-2'-pyrroyloxymethyl]-10α-methoxyergoline maleate, melting at 85°–87°C. Yield 46%.

EXAMPLE 19

1,6-Dimethyl-8β-[4'-methoxy-3'-pyrroyloxymethyl]-10α-methoxyergoline

Operating as in Example 6, but employing 4-methoxypyrrole-3-carboxylic acid, there was obtained 1,6-dimethyl-8β-[4'-methoxy-3'-pyrroyloxymethyl]-10α-methoxyergoline, melting at 214° – 216°C. Yield 49%.

EXAMPLE 20

1,6-Dimethyl-8β-[2'-methyl-3'-pyrroyloxymethyl]-10α-methoxyergoline

Operating as in Example 6, but employing 2-methyl-pyrrole-3-carboxylic acid, there was obtained 1,6-dimethyl-8β-[2'-methyl-3'-pyrroyloxymethyl]-10α-methoxyergoline, melting at 232°–234°C. Yield 73%.

EXAMPLE 21

1,6-Dimethyl-8β-[2', 4'-dimethyl-3'-pyrroyloxymethyl]-10α-methoxyergoline

Operating as in Example 6, but employing 2,4-dimethylpyrrole-3-carboxylic acid, there was obtained 1,6-dimethyl-8β-[2', 4'-dimethyl-3'-pyrroyloxymethyl]-10α-methoxyergoline, melting at 211° – 213°C. Yield 57%.

EXAMPLE 22

1,6-Dimethyl-8β-[4'-methoxy-2'-pyrroyloxymethyl]-10α-methoxyergoline

Operating as in Example 6, but employing 4-methoxypyrrole-2-carboxylic acid, there was obtained 1,6- dimethyl-8β-[4'-methoxy-2'-pyrroyloxymethyl]-10α-methoxyergoline, melting at 176° – 177°C. Yield 63%.

What is claimed is:
1. 1,6-Dimethyl-8β-[2'-methyl-3'-pyrroyloxymethyl]-10α-methoxyergoline or the maleate thereof.
2. 1,6-Dimethyl-8β-[3', 5'-dimethyl-2'-pyrroyloxymethyl]-10α-methoxyergoline or the maleate thereof.
3. 1,6-Dimethyl-8β-[1', 3', 5'-trimethyl-2'-pyrroyloxymethyl]-10α-methoxyergoline or the maleate thereof.
4. 1,6-Dimethyl-8β-[1'-ethyl-2'-pyrroyloxymethyl]-10α-methoxyergoline or the maleate thereof.

* * * * *